(12) United States Patent
Gallili et al.

(10) Patent No.: US 7,192,588 B2
(45) Date of Patent: *Mar. 20, 2007

(54) VACCINE COMPOSITION AND METHOD OF USING THE SAME

(75) Inventors: Gilad Gallili, Jerusalem (IL); Norbert Frydman, Ramat Gan (IL)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/167,329

(22) Filed: Jun. 10, 2002

(65) Prior Publication Data

US 2003/0059435 A1 Mar. 27, 2003

Related U.S. Application Data

(60) Division of application No. 09/795,792, filed on Feb. 28, 2001, now Pat. No. 6,592,869, which is a continuation-in-part of application No. 09/642,913, filed on Aug. 21, 2000, now Pat. No. 6,541,001.

(60) Provisional application No. 60/150,514, filed on Aug. 24, 1999.

(51) Int. Cl.
*A61K 39/00* (2006.01)
*C12K 1/70* (2006.01)

(52) U.S. Cl. .................. 424/184.1; 424/214.1; 424/204.1; 424/222.1; 424/234.1; 424/93.1; 424/464; 435/5

(58) Field of Classification Search ............ 424/184.1, 424/214.1, 204.1, 222.1, 234.1, 93.1; 435/5
See application file for complete search history.

(56) References Cited

U.S. PATENT DOCUMENTS

| | | | |
|---|---|---|---|
| 3,317,393 A | 5/1967 | Chanock et al. | |
| 3,458,621 A | 7/1969 | Tint | |
| 3,603,030 A | 9/1971 | Tint | |
| 3,893,280 A | 7/1975 | King et al. | |
| 4,235,871 A | 11/1980 | Papahadjopoulos et al. | |
| 4,235,876 A | 11/1980 | Gits et al. | |
| 4,251,509 A | 2/1981 | Hanson et al. | |
| 4,458,630 A | 7/1984 | Charma et al. | |
| 4,578,270 A | 3/1986 | Csizer et al. | |
| 5,178,882 A | 1/1993 | Kossovsky et al. | |
| 5,206,219 A | 4/1993 | Desai | |
| 5,336,666 A | 8/1994 | Neway et al. | |
| 5,350,741 A | 9/1994 | Takads | |
| 5,397,569 A | 3/1995 | Whitfill et al. | |
| 5,472,710 A | 12/1995 | Klokkers-Bethke et al. | |
| RE35,338 E | 9/1996 | Haynes | |
| 5,576,014 A | 11/1996 | Mizumoto et al. | |
| 5,587,180 A | 12/1996 | Allen, Jr. et al. | |
| 5,593,697 A | 1/1997 | Barr et al. | |
| 5,631,010 A | 5/1997 | Mekalanos | |
| 5,635,210 A | 6/1997 | Allen, Jr. et al. | |
| 5,709,861 A * | 1/1998 | Santiago et al. | 424/194.1 |
| 5,710,041 A | 1/1998 | Moorman et al. | |
| 5,766,602 A | 6/1998 | Xiong et al. | |
| 5,871,748 A | 2/1999 | Whitfill et al. | |
| 5,897,852 A | 4/1999 | Wilderbeek et al. | |
| 6,541,001 B1 * | 4/2003 | Gallili et al. | 424/184.1 |
| 6,592,869 B2 * | 7/2003 | Gallili et al. | 424/184.1 |

FOREIGN PATENT DOCUMENTS

| | | |
|---|---|---|
| DE | 2237783 | 2/1974 |
| DE | 117250 | 6/1974 |
| DE | 289200 | 1/1976 |
| DE | 106660 | 6/1976 |
| DE | 289201 | 4/1999 |
| DE | 298202 | 4/1999 |
| EP | 0290197 | 9/1988 |
| EP | 0905141 | 3/1999 |
| FR | 2082760 | 3/1970 |
| GB | 0929377 | 6/1963 |
| RU | 2 1 122 429 | 11/1998 |
| WO | WO 91/04749 | 4/1991 |
| WO | WO 9104757 | 4/1991 |
| WO | WO96/01874 | 1/1996 |
| WO | WO 9733531 | 9/1997 |
| WO | WO97/39762 | 10/1997 |
| WO | WO 9813029 | 4/1998 |
| WO | WO 9913869 | 3/1999 |
| WO | WO 9921579 | 5/1999 |
| WO | WO 9938529 | 8/1999 |
| WO | WO 00/48662 | 8/2000 |
| WO | WO 01/12797 | 2/2001 |

OTHER PUBLICATIONS

Gallili et al., Newcastle Disease Vaccines, Biotechnology Advances, vol. 16, No. 2, pp. 343-366, 1998.*

(Continued)

*Primary Examiner*—Stacy B. Chen
(74) *Attorney, Agent, or Firm*—John P. White; Cooper & Dunham LLP

(57) ABSTRACT

The present invention relates to a stable compacted, compressed or hard tableted injectable composition, including a vaccine composition comprising at least one freeze dried antigenic component and a dissolution aid. A package containing the above injectable composition and method to facilitate immunizing a subject against a disease comprising the steps of first dissolving the compacted, compressed or hard tableted vaccine composition in a package with a diluent to form a vaccine solution, and administering the resulting vaccine solution in an amount effective for immunizing is also provided.

13 Claims, No Drawings

OTHER PUBLICATIONS

Worthington et al. (2000) Vaccine 21:1355-1362.*
Embrex Inc. (2001) InOvation™ 1(1):1-2.*
Fahey et al., (1992) Status of Immune-Based Therapies in HIV Infection and AIDS, *Clin. Exp. Immunol.* 88:1-5.
Fox, (1994) No Winners Against AIDS, *Bio/Technology* 12:128.
Haynes et al., (1996) Update on the Issues of HIV Vaccine Development, *Ann. Med.* 28:39-41.
Mattson, Microscale Gas Chemistry: Experiments with Hydrogen Cholride, http://www.mattson.creighton.edu/HC1/,Apr. 21, 1998, see experiment 7 pp. 9-10 (Exhibit 1).
Cardamone, M., et al, "In Vitro Testing Of A Pulsatile Delivery System And Its In Vivo Application For Immunisation Against Tetanus Toxoid", Journal Of Controlled Release, (1997) vol. 47, No. 3.
Haddad, E., et al., "Efficacy Of A Novel Infectious Bursal Disease Virus Immune Complex Vaccine In Broiler Chickens" Avian Diseases, (1997) vol. 41, No. 4, pp. 882-889.
Jeurissen, S., et al., "The Working Mechanism Of An Immune Complex Vaccine That Protects Chickens Against Infectious Bursal Disease", Immunology, (1998) vol. 95, No. 3, pp. 494-500.
Johnston, P., et al., "Applications In *in ovo* Technology", Poultry Science, (1997) vol. 76, No. 1, pp. 165-178.
Kelemen, M., et al., "Pathological And Immunological Study Of An In Ovo Complex Vaccine Against Infectious Bursal Disease", Acta Veterinaria Hungarica, (2000), vol. 48, No. 4, pp. 443-454, Abstract only.
Supplemental European Search Report issued Feb. 28, 2005 in connection with European Application No. EP 02733085.1.

* cited by examiner

VACCINE COMPOSITION AND METHOD OF USING THE SAME

This application is a divisional of U.S. Ser. No. 09/795,792, filed Feb. 28, 2001 now U.S. Pat. No. 6,592,869, which is a continuation-in-part and claims priority of U.S. Ser. No. 09/642,913, filed Aug. 21, 2000 now U.S. Pat. No. 6,541,001, which claims the benefit of U.S. Provisional Application No. 60/150,514, filed Aug. 24, 1999. The contents of the above-identified applications are hereby incorporated by reference into this application.

Through this application, various references are identified by authors and full citations. Disclosure of these publications in their entireties are hereby incorporated by reference into this application to more fully describe the state of the art to which this invention pertains.

FIELD OF THE INVENTION

The present invention relates to a stable compacted, compressed or tableted vaccine composition having a dense solid form, comprising one or more freeze dried (lyophilized) antigenic components and a dissolution aid. This stable dense vaccine composition retains all of the advantageous properties of the lyophilized components thereof, including titer stability and solubility while further providing complete and rapid dissolution in a diluent. Moreover, the vaccine composition of the present invention avoids the disadvantages of prior known lyophilized preparations. A method for immunizing a subject using the stable vaccine composition to form a vaccine solution is also provided.

BACKGROUND OF THE INVENTION

It is well-known, that biological materials in solutions such as vaccines are susceptible to varying influences including heat, oxidizing reagents, salts, pH, light, and proteolitic enzymes.

Several methods are known for reducing these detrimental effects in general and more specifically to improve the stability of a vaccine especially during storage. For example, storage below 0° C., and as low as −70° C., in a freezer is a well-known method. At even lower temperatures, e.g. in liquid nitrogen, many biological materials including living cells can successfully be stored for many years. However, such methods are not always convenient in those situations, for example, that involve the innoculation of free-ranging livestock.

Lyophilizing or freeze drying is another known way of conserving live cells and viruses for use as vaccines. During freeze drying, the solution containing the biological material is first frozen and the water is then evaporated by sublimation, usually under high vacuum and sub-zero temperatures. Previous approaches have used freeze drying or other techniques to formulate viral vaccines but still pose other difficulties with respect to preparation and administration of a stable final dosage form.

For example, U.S. Pat. No. 4,251,509 (Hanson and Abegunde) discloses a stable particulate viral vaccine intended to be orally administered to free ranging livestock in a dry state. However, the disclosed dosage form is not freeze dried but prepared by concentrating and extruding a paste dried to form pellets.

Antioxidants, the selection of which will depend on the particular virus, are required to promote thermostability. Such a formulation may be more complicated to prepare and is not particularly well-suited for those instances when it is desired to dissolve the vaccine before immunization.

U.S. Pat. Nos. 3,458,621 and 3,608,030 (Tint) disclose the use of freeze dried virus preparations to prepare a tablet for oral administration for the immunization of the intestinal tract. However, the tablets prepared are for oral administration and are provided with an enteric coating to delay disintegration. During in-vitro testing they did not rapidly disintegrate and were found to disintegrate only "within 25 minutes" with simulated intestinal fluid. Moreover, the time to disintegrate was measured in simulated intestinal fluid thereby discounting effects of the enteric coating. In addition, Tint further emphasizes that unless the tablets are "press coated" they will lose their titer as shown by a comparison between press coated and non-press coated tablets. Tint notes that the non-press coated tablets "not only failed to elicit an antibody response in all the antibody-negative individuals, but, in addition, the magnitude of the titer rise was significantly smaller." (See column 4, line 40).

PCT Publication No. WO 99/21579 (Seager, et al.) assigned to the R.P. Scherer Corp. discloses a "fast" dispersing composition for a veterinary vaccine such as against New Castle disease that is freeze dried and "loosely compacted."

The dosage form is disclosed as an "open matrix network", such as a "solid toam" referenced from U.S. Pat. No. 4,371,516 (counterpart to UK Patent No. 1,548,022), as opposed to a compressed form or hard tableting. Moreover, the vaccines are directed to oral administration and targeted towards retention at mucosal tissue. Adjuvants serve to provide sufficient residence time for absorption thereon. The disclosed vaccine formulation does not provide for preparation of a liquid dosage for later immunizing, nor a means to readily form a stable, measured vaccine solution for administration as a liquid dose, nor for providing a stable compressed or hard tableted lyophilisate to facilitate later administration thereof.

U.S. Pat. No. 5,587,180 (Allen, Jr. et al) describes a process for making a particulate support matrix for a rapidly dissolving tablet. The process teaches away from freeze drying and uses standard spray-drying techniques. The particulate support matrix is suitable for dosage administration when placed into the oral cavity. Moreover, no stable vaccine formulation is provided as a vaccine solution in a liquid dosage form.

U.S. Pat. No. 5,336,666 (Neway et al.) discloses a freeze dried liquid vaccine that may form a tablet to be reconstituted in liquid form. However, the vaccine is limited to a polar glycopeptide of a particular bacterium and does not provide for complete or rapid dissolution.

Although freeze drying of biological material can be performed according to lyophilizing procedures well known to one skilled in the art to provide a stable vaccine preparation, the titer of a live virus at the end of lyophilization is typically not the same as it was for the solution before the lyophilization process. In general it is not possible to conduct titration before lyophilization as the solution is not stable until it is freeze dried. In addition, the titer will change unpredictably during lyophilization. Consequently, an estimate for the initial titer based on experience is only validated by titration after freeze drying. As a result of all of the above, it is almost impossible to achieve a defined accurate target titer.

If lyophilization has been carried out with the lyophilisate already contained in vials, reworking of the batch is typically not possible, and in some cases a whole batch must be discarded if it is not up to specification.

U.S. Pat. No. 5,897,852 (Wilderbeek, et al.) attempts to solve such a problem using different "freeze dried bodies" with "lyospheres" to make up for shortfalls in the titer of a lyophilized cake. However, each lyosphere has its own titer thereby necessitating the titration of multiple bodies to arrive at a desired titer. Even in the best case, this method does not achieve the exact required titer as it is only an approximation due to the use of combined bodies to achieve the target titer. Furthermore, the production of lyospheres is relatively difficult compared with the more straightforward freeze drying of solutions to produce a cake or powder. Additionally, a special matrix is often required to prevent the lyosphere material from being pulverized after drying. In general, the method requires the preparation of separate solutions each having a different titer, additives and adjuvants. The method does not solve the problem that the titer for a batch of live virus is rarely homogenous, and varies from one vial to the next, particularly over the areas of the cold plates in the lyophiliser. Therefore, determination of the number of lyospheres needed per vial is always an approximation.

Freeze drying may also be useful for vaccines comprising more than one immunogenic component. For example, EP 290197A discloses a freeze dried tetravalent vaccine. The procedure discloses the mixing and subsequent freeze drying of four live virus vaccine components.

A disadvantage to current freeze drying techniques for vaccine preparation is that the process is very complex, having many variables, rendering it notoriously difficult to perform in a reproducible manner to achieve acceptable product and dosage uniformity. This is especially problematic for veterinary vaccines where a large number of doses are freeze dried in one vial. The problem is less common for human vaccine preparation, although equally appreciable where mass innoculation is necessary, for example in military scenarios, or in situations of pandemic infection. For example, a typical single vaccine vial for poultry vaccination comprises either 1000 or 2000 doses, and is registered as such. Before freeze drying, a rough estimation is made about the titer of the material, but the final titer can only be determined after freeze drying, as the titer often decreases rather unpredictably during freeze drying. Furthermore, the raw material of live virus or bacteria cannot usually be kept stable long enough to obtain accurate titer results before freeze drying.

In practice, a container originally comprising more than 2000 doses can often turn out to comprise only 1900 doses after freeze drying. In that case, the vial might only be marketable as a 1000 dose vial, since that typically is the only other official registrable dosage. For such a scenario, a 47% waste of material and corresponding increase in costs could occur. This problem is compounded with combination vaccines because the dosage of the component with the lowest titer must be used to characterize the entire batch. As a further disadvantage, when vials intended to provide 2000 single doses are subsequently marketed as 1000 dose vials and used to innoculate 1000 animals, the animals thus dosed are unnecessarily over-exposed. Moreover, deliberately increasing the number of doses before freeze drying is not a satisfactory alternative when some of the vaccine batch is dried more efficiently. In that situation, one simply ends up wasting that material.

These problems will become increasingly important to solve as Registration Authorities currently work toward a registration system where the number of vaccine dose titers are set between well-defined upper and lower limits. Given the many variables in both the production and the freeze drying process, it will be difficult to meet these limits on a large-scale production basis. As indicated, this problem will be even more pronounced when a combination vaccine is required.

Yet a further disadvantage to previous freeze dried combination vaccines is that a large number of formulated combinations must be kept in storage. This occurs because the various components in a combination vaccine are typically mixed prior to freeze drying. Thus, for the preparation of a full range of single/multi-component-vaccines against, e.g. two diseases, three different products must be kept in stock; (1) the product comprising anti-A vaccine, (2) the product comprising anti-B vaccine; and (3) the product comprising anti-A and anti-B vaccine. In the case of vaccines against three diseases, seven different vaccines/combinations have to be made and stored. For four diseases, this number mounts to fifteen different vaccines/combinations. Consequently, it is often necessary to provide and maintain a large storage capacity.

U.S. Pat. Nos. 5,397,569 and 5,871,748 (Whitfill et al.) disclose a method for producing active immunity against Newcastle Disease virus (NDV) in avian subjects by administering, in-ovo, a vaccine complex comprised of a live vaccine virus and neutralizing antibodies bound thereto. Whitfill discloses that the ratio of virus to the neutralizing antibody or fragment thereof will determine the success of the immunization. However, for such a method to be applied effectively against NDV, a narrow range of values for that ratio must be maintained so that successful immunization will occur without killing the chicks. Moreover, the unpredictability in the titer using lyophilized NDV (as with other virus preparations) means that methods such as Whitfill's are not easily applicable for NDV. Therefore, a method which could ensure more exact titers of NDV and antibodies for preparing such a vaccine is desired.

Yet another disadvantage to prior vaccine formulations and their methods of production lie in the space-consuming nature of the actual freeze drying process. Typically, lyophilizing a vaccine first requires dispensing the solubilized vaccine into glass vials. The vials are then loosely capped with rubber stoppers and placed on trays in racks in a freeze drying chamber or condenser. It is difficult to concentrate very high doses of solubilized vaccine material in a very small volume.

As a result, the vials typically used in freeze drying for multiple vaccine doses always contain a relatively large volume of fluid. Efficient freeze drying requires that the fluid to be lyophilized exposes a large surface area to the vacuum. Therefore, since only the top of the frozen pellet is in contact with the vacuum, vaccines are freeze dried in relatively large glass bottles or vials, with a wide bottom. These vials are sometimes 5 centimeters high, wherein an additional 2 cm of height is needed for the rubber stoppers. Consequently, the ratio of product material to empty space in the freeze drying apparatus is extremely inefficient leading to a less cost effective production process.

Another disadvantage to conventional compositions for freeze dried vaccines formulated to be contained in glass vials is that the rubber stoppers can hinder free transfer of water molecules from the vial to the condenser during lyophilization. This can increase the partial pressure of sublimating gases inside the vial, thereby decreasing the efficiency of the lyophilization, as well as increase the risk of collapse of the lyophilized material. Glass also impedes heat transfer to further affect lyophilization efficiency. Formulating a vaccine that would eliminate both glass vials and stoppers by using trays in the lyophilization would increase efficiency. Moreover, freeze drying is very time-consuming. Vaccine components are typically kept just below the freezing point to decrease water sublimation time. However, a longer drying period leads almost inevitably to a decrease of titer. The glassvials with their stoppers and aluminum covers are generally seen as an encumbrance. In production terms they can represent more than 50 percent of the cost of the finished vaccine. In field situations, the diluent must be injected into the vial and the resultant solution extracted and diluted, if necessary for use. This is an inconvenience not always suited to on-site situations, such as in a chicken-shed. It is not uncommon for the operative in these situations to accidentally be selfinjected during this procedure. Yet another disadvantage to such vaccine packaging and preparation is that some of the concentrated solution will remain in the vial. Consequently, it is generally accepted that an overage in the contents is necessary to compensate for non-homogeneity and production losses, as well as losses incurred over storage periods. Glass vials must also be safely disposed of and can result in possible health and environmental hazards.

As a result, use of conventional freeze dried vaccine formulations involve complicated preparation techniques which are costly and difficult to implement in the field. Consequently, such conventional vaccine formulations are not well-suited for vaccinations in underdeveloped countries were economic and field conditions do not allow for costly campaigns, or in the case of mass immunizations which may be needed, such as in the defense of biological warfare, or other potential catastrophes or epidemics.

What is desired, therefore, is a vaccine formulation which obviates the use of glass vials for administration providing a less costly and bulky packaging alternative. What is also desired is a vaccine formulation and method of use which provides greater dosing accuracy and ease of use while maintaining stability, sterility, solubility and homogeneity for both single and multiple vaccine formulations. A vaccine formulation and improved immunizing method which facilitates more accurate, reproducible and efficient administration can provide the advantages of better field performance, increased safety, cost-effectiveness, less waste, and improved environmental compliance.

SUMMARY OF THE INVENTION

Accordingly, it is an object of the invention to provide a vaccine composition and method of immunizing accomplished by simply dissolving a solid, dense stable form of a lyophilized vaccine in a diluent thereby eliminating the need for glass vials, while also allowing for much greater accuracy of dosing and ease of use.

A further object of the invention is to provide a lyophilized live or inactivated vaccine which is compacted, compressed or tableted as a dense stable solid that will retain its potential immunizing capacity during preparation and for the duration required for sufficient shelf-life of a commercial vaccine.

A further object of the invention is to provide a lyophilized live or inactivated vaccine which is compacted, compressed or tableted as a dense stable solid which facilitates formulation of in-ovo vaccine preparations and uses thereof.

A further object of the invention is to provide a lyophilized live or inactivated vaccine which is compacted, compressed or tableted as a dense stable solid which facilitates packaging of vaccines in non-vial containers and use thereof.

Another object of the invention is to provide a vaccine composition and method of immunizing with greater flexibility in the vaccinations that can be formulated and uses thereof.

A further object of the invention is to provide a vaccine composition and method of immunizing which reduces the need for excess vaccine material needed to compensate for the inherent inaccuracies in the titer of the packaged vaccine made according to known methods.

Another object of the invention is to provide a vaccine composition and method of immunizing which allows greater flexibility in the types of vaccine formulations that may be administered.

Yet another object of the invention is to provide a vaccine composition and method of immunizing which faciliates formulation of a multi-dose vaccine solution and uses thereof.

Another object of the invention is to provide a vaccine composition and method of immunizing which facilitates human mass immunization.

Another object of the invention is to provide a vaccine composition and method of immunizing that is suitable and cost-effective for vaccinations in underdeveloped countries, where cost and field conditions do not allow for complicated preparation and costly campaigns.

Yet another object of the invention is to provide a vaccine composition and method of immunizing amenable for use in defense of biological warfare, where mass immunization is a must.

These and other objects may be achieved by the present invention which relates to a stable vaccine composition comprising at least one pre-titrated lyophilized antigenic component and a dissolution aid, wherein the vaccine composition is in the form of a hard tablet. In addition, the present invention also provides a method of immunizing a subject against a disease comprising the steps of: dissolving a vaccine composition wit h a diluent to form a solution, wherein the vaccine composition comprises at least one lyophilized antigenic component and a dissolution aid, wherein the vaccine composition is in the form of a hard tablet, and wherein the vaccine composition provides protection against such disease; and administering the resulting solution to the subject in an amount effective to immunize the subject against the disease.

The invention in its particular features will become more apparent from the following detailed description considered with reference to the accompanying examples. The following description will continue to discuss the problems and solutions offered by the present invention as they pertain to veterinary applications. However, the following should in no way be interpreted as being limited thereto or inapplicable to human vaccination.

DETAILED DESCRIPTION OF THE INVENTION

This invention provides a stable compressed vaccine composition comprising at least one lyophilized antigenic component and a dissolution aid.

In a preferred embodiment of the invention, the vaccine composition is in the form of a hard tablet.

In another preferred embodiment of the invention, the composition dissolves completely and rapidly in water.

In a preferred embodiment of the invention, the composition is sterile.

In a preferred embodiment of the invention, the dissolution aid is an effervescent agent or pair of agents, a disintegrant, a sufactant, or a solubilizer.

In another preferred embodiment of the invention, the effervescent pair comprises a salt and an acid, In another preferred embodiment of the invention, the effervescent pair is citric acid and the salt is a bicarbonate.

In another preferred embodiment of the invention, the vaccine composition comprises a binder and a lubricant.

In yet another preferred embodiment of the invention, the composition disintegrates completely and rapidly in water.

In another embodiment of the invention, the active material is a pre-titrated lyophilizate that is kept under a dry nitrogen atmosphere below a freezing temperature prior to use.

In another embodiment of the invention, the lyophilized component comprises up to 80% by weight of the composition.

In another preferred embodiment of the invention, the vaccine composition is characterized by complete dissolution within less than 80 seconds upon contact with a diluent.

In another preferred embodiment of the invention, complete dissolution of the vaccine composition occurs at a diluent to composition ratio of between 0.5 ml of diluent per 200 mg of composition and 100 ml of diluent per 400 mg of composition.

In another preferred embodiment of the invention, the stability of the vaccine composition is characterized by a loss of titer no greater than the difference between $10^{9.7}\text{EID}_{50}$/ml and $10^{9.2}\text{EID}_{50}$/ml after 5 days at 37° C.

In another preferred embodiment of the invention, the stability of the vaccine composition is characterized by a loss of titer no greater than the difference between $10^{9.7}\text{EID}_{50}$/ml and $10^{9.3}\text{EID}_{50}$/ml after 9 months at 4° C.

In yet another preferred embodiment of the invention, the antigenic component of the vaccine composition is a whole virus, a whole bacterium or a whole microorganism.

In another preferred embodiment of the invention, the antigenic component of the vaccine composition is a live bacterium or a live virus.

In a preferred embodiment of the invention, the vaccine composition comprises an indicator of the presence of the antigenic component.

In a preferred embodiment of the invention, the indicator is a dye.

This invention further provides a stable vaccine composition comprising at least one lyophilized antigenic component and a dissolution aid, wherein the vaccine composition is in the form of a hard tablet and the antigenic component comprises a lipopolysaccharide or a protein, whether naturally occurring, recombinant, or modified.

In a another preferred embodiment of the invention, the antigenic component is a live virus selected from the group consisting of: Newcastle Disease virus or bacterium, Newcastle Disease virus VH strain, Infectious Bursal Disease virus, Gumboro Disease virus, fowl pox virus, Laryngotraecheitis virus, Infectious Bronchitis of poultry virus, Gumboro Winterfield virus, Infectious Bronchitis (IB-H120), sheep pox virus, Rinderpest virus, anthrax spores, *Salmonella* SPP., *E.coli.,* or an admixture of one or more of the foregoing whether naturally occurring, recombinant or modified.

In yet another embodiment of the invention, the antigenic component is selected from the group consisting of: anthrax spores, *Salmonella* SPP, *E. coli,* or an admixture of one or more of the forgoing, whether naturally occurring, recombinant or modified.

In yet another preferred embodiment of the invention, the antigenic component is a live virus and the composition further comprises neutralizing antibodies against the virus.

This invention further provides a method of immunizing a subject against a disease comprising the steps of: dissolving a vaccine composition with a diluent to form a solution, wherein the vaccine composition comprises at least one lyophilized antigenic component and a dissolution aid, wherein the vaccine composition is in the form of a hard tablet, and wherein the vaccine composition provides protection against such disease; and administering the resulting solution to the subject in an amount effective to immunize the subject against the disease.

In a preferred embodiment of the invention, the dissolving step of the method of immunizing is further characterized by complete dissolution of the vaccine composition.

In yet another preferred embodiment of the invention, complete dissolution during the dissolving step of the method of immunizing occurs at a diluent to composition ratio of between 0.5 ml of diluent per 200 mg of composition and 100 ml of diluent per 400 mg of composition.

In another preferred embodiment of the invention, the dissolving step of the method of immunizing is further characterized by complete dissolution within less than 80 seconds upon contact with a diluent.

In another embodiment of the invention, the administering step comprises injecting the subject with the solution.

In another embodiment of the invention, the administering step comprises spraying the subject with an aerosol formed from the solution.

In yet another embodiment of the invention, the administering step comprises applying the solution to the subject in the form of eye drops.

In yet another embodiment of the invention, the administering step comprises applying the solution by oral ingestion.

In a preferred embodiment of the invention, the method of immunizing is applied to a subject that is an avian animal and the disease is selected from the group consisting of Newcastle Disease, Infectious Bursal Disease, fowl pox, Laryngotracheitis, Infectious Bronchitis of poultry.

In another preferred embodiment of the invention, the administering step comprises administering a solution to the subject in-ovo.

This invention also provides a package comprising the vaccine composition having at least one lyophilized antigenic component and a dissolution aid, wherein the vaccine composition is in the form of a hard tablet or further comprises an indicator of the presence of the antigenic component.

In a preferred embodiment of the invention, the package is a blister pack.

In another preferred embodiment of the invention, the package is a sterile syringe.

This invention also provides a sterile syringe comprising a compacted vaccine composition, wherein the vaccine composition comprises at least one lyophilized antigenic component and a dissolution aid.

In one embodiment of the invention, the compacted vaccine composition of the sterile syringe is a compressed composition.

In a preferred embodiment of the invention, the compressed vaccine composition of the sterile syringe is in the form of a hard tablet.

This invention further provides a method of immunizing a subject against a disease which comprises adding a diluent to a sterile syringe comprising a compacted vaccine composition, wherein the vaccine composition comprises at least one lyophilized antigenic component and a dissolution aid, or wherein the compacted vaccine composition of the sterile syringe is further characterized as a compressed composition, or wherein the compressed vaccine composition of the sterile syringe is in the form of a hard tablet, so as to form a solution in the syringe and administering the resulting solution to the subject.

Solutions resulting from dissolution of the vaccine composition of the present invention may be administered by any suitable means. The method of immunizing a subject against a disease according to the present invention may employ a number of methods to administer a liquid solution formed by the vaccine composition. Exemplary methods of administration are intramuscular injection, subcutaneous injection, intravenous injection, intra peritoneal injection, eye drop, via drinking water, aerosol, or nasal spray. When the animal to be treated is a bird, the bird may be a newly hatched (i.e., about one day old after hatching), adolescent, or adult bird. The vaccine of the present invention may be useful for administration of birds in ovo, as described in U.S. Pat. No. 4,458,630 to Sharma.

The freeze dried (lyophilized) pre-titrated vaccine composition of the present invention is understood to be a preparation composed of at least one freeze dried antigenic pre-titrated vaccine component, excipients and optionally various additives that have been compacted or compressed into a dense form.

As used herein, "dense" refers to the vaccine composition having a density greater than 1.0 g/cc. Usually, the density of the vaccine composition will be greater than 1.5 g/cc. Typically, the range of density for the vaccine composition will be from about 1.5 g/cc to 2.5 g/cc.

The vaccine composition may be compacted, compressed, or in the form of a hard tablet.

As used herein, "compacted" refers to a vaccine composition having a density greater than 1.0 g/cc, but no measurable hardness as measured in Strong-Cobb Units (SCU) and tested for hardness on a ERWEKA Tablet Hardness Tester Model TBH20.

As used herein, "compressed" refers to a vaccine composition having a hardness of at least 2.0 SCU and "hard tablet" refers to a vaccine composition in the form of a tablet or other dense form having a hardness of at least 3.0 SCU.

The compacted, compressed and hard tablets of the vaccine composition can be made on an instrumented MANESTY F3 Single Punch 12 mm Flat Beveled or 6 mm standard concave punches.

The vaccine composition in the form of a hard tablet was made at a pressures of a maximum of 4 tonnes. The tablets were tested for hardness on a ERWEKA Tablet Hardness Tester Model TBH20 as described above, and were all found to have a hardness greater than 3.0 SCU.

The classic tablet normally associated with therapeutic agents is understood to be such a "tablet". However, it is understood that any compacted or compressed dense form is intended, including those having less frequent use in the pharmaceutical field. For example, large "briquettes" would be suitable should the final application require a large volume of material.

It is understood that a preparation that disintegrates or dissolves "completely" and "rapidly" in a diluent is one that is capable of doing so in pure water even if the intended use is not with pure water, but rather with a solution e.g., saline, or for that matter a non-aqueous vehicle.

By "completely dissolved" it is understood that no soluble component is left undissolved. By "rapidly disintegrated or dissolved" is understood that disintegration or dissolution is complete within approximately a few minutes or less when a large volume of water is employed for small volume of compressed lyophilized vaccine composition e.g., 100 ml of water for a 400 mg effervescent tablet. The time is increased where the volumes of diluent are comparably decreased. Thus the same tablet might require 70 seconds with a volume of water of 10 ml, and 80 seconds in 2 ml of water.

The disintegration or dissolution time referred to above is the time taken for dissolution or disintegration of a tablet when placed in a measured quantity of water at room temperature without stirring.

By "stable" it is understood that the compositions of the present invention will maintain their (potential) immunizing capacity during preparation and for the duration required for shelf life of a commercial vaccine.

As will be demonstrated by reference to the following examples, a vaccine composition and method of immunization according to the present invention has numerous advantages as has been described herein.

The method of the present invention is generally exemplified as follows for the preparation of a vaccine composition containing 1000 doses of vaccine component. A solution of the vaccine component is lyophilized in trays. The dried material is pulverized. The titer of a homogeneously mixed sample after freeze drying is determined while the lyophilizate is kept under nitrogen in a tightly secured container at $-20°$ C. If the titer of the lyophilized material is determined to be 625 doses per 100 mg, it suffices to weigh out 160 mg of this material per compressed vaccine preparation to arrive exactly at the required titer. The material is then mixed with optional and/or functional additives and the preparation is compressed or tableted. The compressed freeze dried vaccine preparations can then be packaged by any of the methods known to those skilled in the art and/or described herein.

The term excipient is a catch-all term for diluents or vehicles used in the formulation of the vaccine composition. Excipients can include: diluents or fillers, binders or adhesives, dissolution aids, lubricants, antiadherents, glidants or flow promoters, colors, flavors, sweeteners and adsorbents.

Specifically, tablet fillers are substances that compromise the bulk of the tablet and primarily act as a carrier. Typical tablet fillers include, but are not limited to, calcium sulfate, calcium phosphate, calcium carbonate, starch, modified starches (carboxymethyl starch, etc.), microcrystalline cellulose, lactose, sucrose, dextrose mannitol and sorbitol.

Tablet filler levels are from about 0% to 90% by weight of the tablet.

Binders act as the "glue" which holds powders together to form granules. Binders include, but are not limited to, natural polymers such as starches or gums acacia, tragacanth and gelatin or synthetic polymers such as PVP and methyl-, ethyl- and hydroxypropylcellulose.

Binder levels are from about 0% to 20% by weight of the composition.

Dissolution aids promote dissolution of the vaccine composition. Typical examples include, but are not limited to effervescent agents, disintegrates, surfactants and solubilizers.

Disintegrants cause compressed tablets to break apart. Typical examples include, but are not limited to, starch, microcrystalline cellulose, purified wool starch, alginic acid, sodium starch glycolate guar gum, crosslinked polyvinyl pyrolidone (PVP), ion exchange resin and celluloses such as methyl-, croscarmellose sodium, sodium carboxymethyl- and hydroxypropylmethyl-.

Dissolution aid levels are from about 1% to 95% by weight of the composition.

Lubricants reduce friction between the material to be compressed and die wall during compression and ejection. Most lubricants are water insoluble and include stearates (magnesium, calcium and sodium), stearic acid, talc and waxes. Water soluble lubricants include PEG's, sodium benzoate, sodium oleate, sodium acetate, sodium lauryl sulfate and magnesium lauryl sulfate.

Lubricant levels are from about 0% to 5% by weight of the composition.

Colorants are added to help identify types of vaccine formulations such as in the form of tablets for aesthetic and functional purposes, for example and not as limitation to the present invention, the dyes disclosed in Examples A through D taken from Israeli Patent No. 46189.

Colorant levels are from about <1% of the formulation.

The vaccine compositions of the present invention can be tableted according to methods known to those skilled in the art, such as described in Pharmaceutical Dosage Forms, Tablets, 2nd. Ed. 1989, Vols 1, 2, 3, Editors H. A. Lieberman, L. Lachman, J. B. Schwartz.

In a preferred embodiment, the composition of the present invention is a hard tablet prepared having an effervescent agent as a dissolution aid. As those skilled in art appreciate, the effervescent tablet must contain a basic component and an acidic component, such as an effervescent pair, so that upon dissolution appropriate reactions occur to generate carbon dioxide and carbonic acid. Suitable effervescent components include the carbonate family of basic compounds and inorganic or organic acidic compounds.

Among the carbonate family of basic compounds, preferred effervescent agents for use in the compositions of the present invention are sodium carbonate, sodium bicarbonate, glycine carbonate, potassium carbonate, potassium bicarbonate, potassium dihydrogencitrate, and calcium carbonate. A most preferred basic compound is sodium bicarbonate.

Preferred acidic components for use in the compositions of the present invention are citric acid, adipic acid, tartaric acid, maleic acid, boric acid, benzoic acid, hydroxybenzoic acid, methoxybenzoic acid, mandelic acid, malonic acid, lactic acid, pyruvic acid, glutaric acid, aspartic acid, hydrochloric acid, oxalic acid, salicylic acid, succinic acid, and acetic acid. A most preferred acidic effervescent component is citric acid.

In addition to the basic and acidic effervescent tablet ingredients described above, the tablet composition of the present invention may also contain other excipients conventionally employed.

The tablet compositions of the present invention are obtained using tableting procedures known in the art. Generally, the tableting procedures used for the present invention may be summarized as follows: the ingredients were sieved, blended and directly compressed into tablets of the required weight, size and hardness on a MANESTY F3 tablet press.

The effervescent tablet compositions of the present invention may be dissolved in ordinary water or a simple saline solution.

Antigenic vaccine components are those components that specifically trigger the immune response against the antigen or antigens from which the vaccine components were derived.

Such components may originate from one virus or microorganism including recombinants e.g. an antigenic lipopolysaccharide and an antigenic protein, or e.g., two different antigenic proteins. They may also comprise antigenic parts of the protein or polysaccharide. These components are generally referred to as subunit components. In some cases the vaccine component comprises the whole virus or microorganism including recombinants. The vaccine component can for example be a bacterin, or a live attenuated bacterium or virus, an inactive bacterium or virus, or a dead bacterium or virus including recombinant and otherwise modified. Preferably, a vaccine component is a live (modified nonvirulent or partially virulent including recombinant) bacterium or virus. Examples include, but are not limited to, *Salmonella* bacteria, New Castle disease virus, Infectious Bursal Disease (Gumboro) virus, Infectious Bronchitis virus, Pseudorabies virus or anthrax spore vaccine.

Combination vaccines are vaccines comprising various vaccine components. Combination vaccines may also comprise antigenic components drived from two or more different viruses or microorganisms.

More complex combinations are also possible. Thus, vaccines of one of the types described above, as well as mixtures thereof are referred to as combination vaccines. These can also contain any of the known adjuvants.

A "package" is understood to be any package useful for the storage of a stable compressed vaccine preparation.

The package may, for example and not as a limitation, be a glass or plastic (e.g., a high-density polyethylene) container generally used for packaging and storage of tablets. Adding the stable compressed freeze dried vaccine preparation to a diluent to homogeneously dissolve the preparation would suffice to make the vaccine ready for use. Another form of packaging for compressed freeze dried vaccine preparations of the subject invention is a blister pack. One example of a blister pack are plastic sheets, with rows of pits (trays) which contain the preparations and are heat sealed with aluminum foil lidding preferably under dry nitrogen. Another variety of blister pack useful for sensitive products are so-called aluminum/aluminum blisters where both tray and lidding are based on aluminum or aluminum laminates with various plastics. This would avoid the use of expensive and space consuming glass vials, generally used for packaging and storage of vaccines for which the eventual user generally has no use.

The present invention makes it possible to add one or more compressed freeze dried vaccine compositions directly from a blister pack to e.g., a bucket of water to be used in the drinking water or aerosol spraying system to ensure successful vaccination. This is usually accomplished on-site, for example in a chicken shed. Veterinary vaccination can also be achieved by fogging, vent brush, piercing, whole body spray or as eye drops. The vaccine solution obtained in a similar manner might be used alternatively for in-ovo immunization of embryos as described in U.S. Pat. Nos. 5,397,569 and 5,871,748.

It is clear that any device that can be used to contain compressed solids can be used in the invention. A diluent may be just water, or on the other hand it may be a complex mixture of buffers and adjuvants. This will depend mainly on which additives have been added to the solution prior to lyophilization or to the preparation prior to compression.

Known freeze drying methods yield a cake comprising the vaccine component or components in a vial. This method is space and time-consuming, as mentioned. If the antigenic vaccine component or components are freeze dried in trays of solution, then the whole surface of the cold plates in the freeze drying machine is utilized during the process. Additionally, should collapse occur, or for that matter if there is any other problem in the freeze drying process, the material can be easily recovered. This is not the case if the material was pre-filled into glass vials prior to lyophilization. Additionally, since no height consuming vials are involved in this part of the process, the cold plates can be stacked up to a high-density. As a result, the capacity of freeze dryers substantially increases, limited practically only by condenser capacity. As a corollary, much smaller freeze dryers could be used for the present invention to achieve the same output as when vials are used in much larger dryers.

Therefore, in one preferred embodiment, the vaccine composition is compressed from sterile lyophilized antigenic material which has been dried in trays and then broken into powder and admixed with sterile additives to aid tableting and eventual dissolution. The sterile vaccine composition is then packaged under dry nitrogen gas in a sterile blister strip pack with a high moisture and gas barrier.

In one preferred embodiment, the lyophilized material is a live attenuated virus.

In another preferred embodiment, an admix comprising a combination of previously dried virus components is compressed into a single preparation together with additives to aid dissolution and optionally those adjuvants desired for inoculation.

If a combination vaccine is required, the advantages offered by the present invention are even more pronounced. It suffices to simply add sufficient pre-titrated lyophilisate of each type of antigenic vaccine component to the preparation before compression to achieve a combination vaccine with each component in a highly accurate dose.

At the same time, the present invention offers a solution to the problem of the large storage capacity needed to store all possible variants of e.g., a three or four component vaccine.

Instead of mixing the various components prior to freeze drying as may be required for the freeze drying of combination vaccines, each component is freeze dried separately. Thus the various components can be stored separately. When necessary, each desired combination is easily made by admixing the appropriate amount of lyophilized material of each desired component into one preparation as described herein, and then compressing and packaging the mixture as described.

This allows for example, in the case of a 4-component combi-vaccine, stocking only four containers, each only containing lyophilized material of one specific vaccine type to compose any single or combination vaccine preparation that is required. Previous methods would require 15 different containers, each comprising a prefabricated component or mixture.

In yet another preferred embodiment, the vaccine container comprises a sterile blister strip containing solid forms, such as sterile tablets compressed from lyophilized material of one or more vaccine components admixed with a sterile dissolution aid in an effervescent pair (e.g., sodium bicarbonate and citric acid) a sterile binder (e.g., polyvinylpyrrolidone) and a sterile lubricant (e.g., sodium stearyl fumarate, magnesium stearate). These single or multiple component preparations can then be used to easily prepare in situ an accurate vaccine solution of known titer. The foregoing are examples for the dissolution aid, binder and lubricant, and are not to be taken as a limitation for the vaccine composition of the present invention.

In yet another embodiment, the vaccine composition and method of immunization comprises a vaccine composition with components derived from two or more antigenic components. A vaccine based on components from multiple antigenic components has the advantage that a single administration of such a vaccine suffices to induce protection against multiple diseases. It should be understood that for each virus or microorganism, any of several different antigenic vaccine components may be included.

In yet a further embodiment, the antigenic components for each vaccine can be mixed in the exact ratios needed to form a complex required for in-ovo immunization such as live Marek's disease, NDV and Gumboro vaccines. Multicomponent in-ovo vaccine preparations are therefore also possible. The dosage form for such a combination can be achieved by the present invention by compressing an admixture of the freeze dried antigenic components for each disease, and the required antibodies together with the tableting aids. Such a preparation could then be used to achieve the desired virus immunizing factor complex in situ by dissolution of the preparation in the required vehicle and under stipulated conditions directly prior to in-ovo inoculation.

Usually, the vaccine container can contain between 1 and 10,000 doses or more of vaccine. Single dose containers are common for individual vaccination, both for human and veterinary use.

Human Poliovirus vaccine, human live freeze dried Typhoid vaccine or Canine Parvovirus vaccine are typically formulated as single dose vaccines. It should be understood, that for a single dose of vaccine, similar formulation procedures as described for multi-dose vaccines fully apply.

For the vaccination of large sheds of newly hatched chickens, it is common practice to use a 10,000 dose vaccine container for mass vaccination against Infectious Bronchitis virus or NDV. For the vaccination of large farm animals such as cattle, against e.g., Infectious Bovine Rhinotracheitis or Parainfluenza virus, vaccine containers with 10 doses are commonly used.

One of the advantages of the vaccine compositions prepared according to the present invention, is that dissolution aids which may have been incompatible in the freeze dried solution, can be included after lyophilization. This speeds the administration procedure. It has unexpectedly been found that the use of citric acid as part of an effervescent pair, which was expected to be detrimental to the live attenuated virus preparations, had no significant impact on the titers.

It should also be apparent that the integrity of the moisture barrier for the container has a significant effect with formulations of this type and steps should be taken to ensure that an effective moisture barrier is formed in the packaging. This is particularly true when employing blister strip packaging and where the additives selected are potentially destabilizing when wet, as is the case with citric acid.

The present invention also provides a method of immunizing a subject against a disease comprising the steps of: dissolving a vaccine composition with a diluent to form a solution, wherein the vaccine composition comprises at least one lyophilized antigenic component and a dissolution aid, wherein the vaccine composition is in the form of a hard tablet, and wherein the vaccine composition provides protection against such disease; and administering the resulting solution to the subject in an amount effective to immunize the subject against the disease.

Alternatively, the lyophilisates may comprise antigenic vaccine components which were derived from two or more viruses or microorganisms.

In addition, the present invention provides a vaccine composition wherein the vaccine composition and a diluent are contained together in a package. Such an embodiment allows for a method of immunization where a dissolving step to form a liquid vaccine for administration can occur in situ in the field.

It should be understood that a vaccine package or pack containing the compressed freeze dried stable vaccine composition may be any useful packaging of a vaccine. In a simple form, the vaccine pack comprises a vaccine container comprising the vaccine components, packed together with instructions in a box. In a more complex form of a vaccine pack, the vaccine container could additionally comprise a diluent and a syringe. In an additional embodiment, the compressed lyophilized vaccine is packed under sterile conditions into a sealed syringe, where the dissolution of the vaccine can thus occur inside the sterile syringe. In this way the batch size of pre-filled syringes is not dependent on the space occupied by syringes in the lyophilizer.

The following examples illustrate preparation and potency of the vaccine composition of the present invention when used to immunize a subject against various infectious diseases. Stability evaluations with a titer analysis of a compressed freeze dried tablet form for various vaccine formulations are also presented.

The examples are presented to further illustrate and explain the present invention and should not be taken as limiting in any regard. Unless otherwise indicated in the examples and elsewhere in the specification and claims, all parts and percentages are by weight. Temperatures are in degrees Centigrade.

EXAMPLE 1

1.1 Preparation of Tablets Comprising Live Attenuated Newcastle Disease Virus VH Strain (Hereinafter NDV-VH)

Fertile, specific-pathogen-free (SPF) eggs were inoculated with NDV and incubated according to known methods for propagation of NDV viruses in eggs.

Allantoic amniotic fluid (AAF) was harvested and purified by centrifugation at 4000 g for 20 min.

Lyophilization in vials was performed fully according to known, standard procedures.

Tablets were prepared in the following manner:

To 13.2 g of pulverized lyophilisate was added:
60 g sodium bicarbonate
42 g citric acid anhydrous
4.2 g polyvinylpyrrolidone K-30
0.3 g magnesium stearate The ingredients were then mixed and tablets were punched each with a weight of 400 mg.

Each resultant tablet thus prepared contained 44 mg of the lyophilizate.

1.2 Analysis of Tablets

The titer in SPF eggs of a random sampling of the tablets was evaluated and compared to the adjusted amount of the lyophilisate in the vials.

| | |
|---|---|
| NDV-VH/tablet | $10^{9.7}$ $EID_{50}$* |
| NDV-VH/vial | $10^{9.6}$ $EID_{50}$ |

*Egg infectious dose 50 units.

When one tablet was added to 100 ml of water, dissolution was complete in less than one minute, i.e. no trace of solid was visible to the naked eye.

When one tablet was added to 10 ml of water, dissolution was complete in 70 seconds.

When one tablet was added to 2 ml of water, dissolution was complete after 80 seconds.

In 1 ml of water, although complete dissolution was achieved, the effervescent nature of this tablet was not found to be involved in the full dissolution, which had taken approximately 4 minutes.

1.3 Packaging and Stability

The tablets were packed in Polyvinyl chloride (PVC) blister strips and stability tested at 37° C. and found to be relatively stable over 5, 7 and 9 day periods.

| | Days at 37° C. | | | |
|---|---|---|---|---|
| | zero | 5 | 7 | 9 |
| NDV-VH tablet | $10^{9.7}$ | $10^{9.2}$ | $10^{9.3}$ | $10^{9.4}$ |

Storage at 4° C. produced no appreciable change in titer and color of tablets after nine months.

| | Months at 4° C. | | |
|---|---|---|---|
| | zero | 3 | 9 |
| NDV-VH tablet | $10^{9.7}$ | $10^{10.1}$ | $10^{9.3}$ |
| NDV-VH vial | $10^{9.6}$ | $10^{9.6}$ | $10^{9.3}$ |

Titers given are in $EID_{50}$ units per tablet or vial calculated for the same amount of active material.

1.4 Potency Test of the Tableted NDV-VH in Chickens

| Group | NDV-VH | $EID_{50}$/ Dose | HI at 3 weeks Post-Vaccination | Mortality after challenge |
|---|---|---|---|---|
| A | tablet 1 | $10^{6.6}$ | 9.3 | 2/18 |
| B | tablet 2 | $10^{6.3}$ | 9.2 | 1/20 |
| C | vial | $10^{6.6}$ | 9.2 | 2/19 |
| D | non-vaccinated | — | 1.2 | 10/10 |

HI = Haemagglutination inhibition units.

A: A tablet of NDV-VH was dissolved in 20 ml of sterile distilled water and 0.02 ml was used to vaccinate each of the 18 chicks (4 weeks old, kept in isolators) by eye drops.

B: Another group of chicks was similarly vaccinated with the tableted VH vaccine dissolved in 40 ml of sterile distilled water.

C: A vial of NDV-VH was dissolved in sterile distilled water to give the same virus concentration as in A.

D: Non vaccinated control.

At three weeks post vaccination the birds were bled for antibodies titration by the Haemagglutination inhibition (HI) test and all the groups were challenged with viscerotropic velogenic NDV given by i.m. Injection at $10^{5.3}$ $EID_{50}$/bird at the Kimron Veterinary Institute (The Israeli Veterinary Services).

The results of the tests indicate that good protection is being provided to the chickens by all the vaccine preparations tested.

EXAMPLE 2

2.1 Preparation of Tablets Comprising NDV-VH

Fertile, SPF eggs were inoculated with NDV and incubated according to known methods for propagation of NDV viruses in eggs.

AAF was harvested and purified by centrifugation at 4000 g for 20 min. Lyophilization was performed fully according to known, standard procedures.

NDV-VH virus was lyophilized in a tray. The dried powder was sealed under low humidity in a sterile double polypropylene bag and kept at −20° C. Effervescent tablets containing increasing contents of dried powder were produced. Tablets were prepared according to the procedure described in Example 1.

| Composition | Wt. (g) | Wt. (g) | Wt. (g) | Wt. (g) |
|---|---|---|---|---|
| VH Lyophilized tray dried | 1.25 (2.7%) | 2.5 (5.3%) | 5.0 (10.1%) | 10.0 (20.3%) |
| Sodium Bicarbonate | 25.0 | 25.0 | 25.0 | 22.0 |
| Citric Acid Anhydrous | 17.5 | 17.5 | 17.5 | 15.4 |
| polyvinyl-pyrrolidone K-30 | 1.75 | 1.75 | 1.75 | 1.75 |
| Magnesium Stearate | 0.12 | 0.12 | 0.12 | 0.12 |
| Tablet weight | 0.5 | 0.45 | 0.38 | 0.36 |

2.2 Analysis of Tablets

NDV-VH titers ($EID_{50}$) in the tablets were obtained by titrations in SPF eggs.

| Percent lyophilisate/tablet | 2.7 | 5.3 | 10.5 | 20.3 |
|---|---|---|---|---|
| NDV-VH/tablet | $10^{8.00}$ | $10^{8.25}$ | $10^{8.75}$ | $10^{9.00}$ |

Satisfactory linear relationship was obtained between active material concentrations and virus titers.

When one tablet was added to 100 ml of water, dissolution was complete in less than one minute, i.e. no trace of solid was visible to the naked eye.

2.3 Packaging and Stability

The tablets were placed in syringes, which were packed in aluminum laminate sachets. An injectable solution was prepared by sucking the diluent for injection into the syringe, followed by complete dissolution of the tablet. The resulting injectable solutions were used either directly, for individual vaccination, or alternatively for multiple vaccination after further dilution in a larger container. An automatic syringe was then applied.

EXAMPLE 3

3.1 Preparation of Tablets Comprising NDV-VH Containing Antibodies Against Newcastle Virus (NDA) for In-Ovo Vaccination Fertile, SPF eggs were inoculated with NDV and incubated according to known methods for propagation of NDV viruses in eggs.

AAF was harvested and centrifuged at 4000 g for 20 min. Lyophilization was performed fully according to known, standard procedures and the lyophilized material titrated. The desired amounts of NDV and NDA were determined.

Tablets were prepared in the following manner:
To 7.0 g of pulverized lyophilisate was added:
0.36 g lyophilized hyperimmune chicken serum for NDV (NDA)
13 g sodium bicarbonate
9.1 g citric acid anhydrous
0.9 g polyvinylpyrrolidone K-30
0.07 g magnesium stearate The ingredients were then mixed and tablets were punched each with a weight of 500 mg. Each tablet thus prepared contained 115 mg of the lyophilized virus preparation.

3.2 Analysis of the Tablets

When one tablet was added to 100 ml of water, dissolution was complete within 2.5 min, i.e. no trace of solid was visible to the naked eye.

3.3 Packaging

The tablets were packed in PVC blister strips.

3.4 Potency Test of Tabletted NDV-VH with NDA In-Ovo

In-ovo vaccination of commercial broiler chicks with NDV-VH+NDA. Challenge of In-ovo vaccinated chicks at 2 and 4 weeks post hatching was conducted. The embryos were injected in a commercial farm by an Inovoject apparatus (Embrex U.S.A.) at 18 days of incubation. A tablet was dissolved in 200 ml of Marek's vaccine diluent and 0.05 ml was injected into each egg. Both vaccinated and non-vaccinated chicks were kept in isolators to avoid non-specific contamination by NDV viruses.

| | HI at 2 weeks | % Mortality at 2 weeks challenge | HI at 4 weeks | % Mortality at 4 weeks challenge |
|---|---|---|---|---|
| Vaccinated | 5.7 | 40 | 4.4 | 10 |
| Non-vaccinated | 3.4 | 53 | 2.5 | 80 |

At 2 and 4 weeks chicks were bled for antibodies detection by the HI test and both groups were challenged with viscerotropic velogenic NDV given by I.M. injection of $10^{5.3}$ $EID_{50}$/bird at the Kimron Veterinary Institute (The Israeli Veterinary Services). The results indicate that good protection was provided to the chicks at 4 weeks post hatching.

EXAMPLE 4

4.1 Preparation of Tablets Comprising Live Attenuated Gumboro Disease Virus (Hereinafter "MB")

SPF eggs were inoculated with Gumboro (MB) disease virus and incubated according to known methods for propagation of viruses in eggs.

Embryos and chorioallantoic membranes were harvested and the virus was extracted by homogenization. Lyophilization was done fully according to known, standard procedures.

Tablets were prepared in the following manner:
To 10.0 g of pulverized lyophilisate was added:
22.4 g sodium bicarbonate
15.7 g citric acid anhydrous 1.7 g polyvinylpyrrolidone K-30

0.1 g magnesium stearate

The ingredients were then mixed and tablets were punched each with a weight of 350 mg.

Each tablet thus prepared contained 70 mg of the lyophilisate.

4.2 Analysis of Tablets

The titer of a random sampling of the tablets was evaluated as $10^{5.6}$ EID$_{50}$/tablet. ($10^{2.5}$ EID$_{50}$ is considered to be a vaccinating dose)

When one tablet was added to 100 ml of water, dissolution was complete in less than one minute, i.e. no trace of solid was visible to the naked eye.

Virus titers in effervescent tablets and vials

| | |
|---|---|
| MB/tablets | $10^{5.6}$ EID$_{50}$ |
| MB/vials* | $10^{5.5}$ EID$_{50}$ |

*Adjusted to the same quantity of immunizing material.

4.3 Packaging and Stability

The tablets were packed in PVC blister strips and stability tested at 37° C.

| | Days at 37° C. | |
|---|---|---|
| | zero | 5 |
| MB | $10^{5.6}$ | $10^{4.9}$ |

EXAMPLE 5

5.1 Preparation of Effervescent Tablets Containing Fowl Pox Live Vaccine Virus

SPF eggs were inoculated with Fowl Pox disease virus and incubated according to known methods for propagation of viruses in eggs.

Embryos and chorioallantoic membranes were harvested and the virus was extracted by homogenization.

Lyophilization was performed fully according to known procedures.

700 mg tablets were prepared substantially as described in Example 1.

Each tablet contained 140 mg of lyophilisate.

5.2 Analysis of Tablets

The titer of each tablet was evaluated in SPF eggs and was found to be $10^{6.25}$ EID$_{50}$/tablet. When one tablet was added to 100 ml of water, dissolution was complete in two minutes, i.e. no trace of solid was visible to the naked eye.

EXAMPLE 6

6.1 Preparation of Effervescent Tablets Containing Laryngotracheitis (Fowl) Live Virus SPF eggs were inoculated with Laryngotrachietis vaccine virus and incubated according to known methods for growing viruses in eggs. Embryos and chorioallantoic membranes were harvested and the virus was extracted by homogenization.

Lyophilization was performed fully according to known procedures. 700 mg Tablets were prepared substantially as described in Example 1.

Each tablet contained 140 mg of lyophilizate. The titer of each tablet was evaluated in SPF eggs and was found to be $10^{5.53}$ EID$_{50}$.

EXAMPLE 7

7.1 Preparation of Effervescent Tablets Containing Infectious Bronchitis of Poultry Live Virus SPF eggs were inoculated with Infectious Bronchitis of Poultry disease virus and incubated according to known methods for growing viruses in eggs. Embryos and chorioallantoic membranes were harvested and the virus was extracted by homogenization.

Lyophilization was performed fully according to known procedures.

700 mg tablets were prepared substantially as described in Example 1.

Each tablet contained 140 mg of lyophilisate.

7.2 Analysis of Tablets

The titer of each tablet was evaluated in SPF eggs and found to be $10^{6.15}$ EID$_{50}$/tablet.

EXAMPLE 8

8.1 Preparation of Effervescent Tablets Containing Gumboro Winterfield (Fowl) Live Virus SPF eggs were inoculated with Gumboro Winterfield (Fowl) disease virus and incubated according to known methods for propagating viruses in eggs.

Embryos and chorioallantoic membranes were harvested and the virus was extracted by homogenization.

Lyophilization was performed fully according to known procedures.

700 mg tablets were prepared substantially as described in Example 1.

Each tablet contained 140 mg of lyophilizate.

8.2 Analysis of Tablets

The titer of each tablet was evaluated in SPF eggs and found to be $10^{6.28}$ EID$_{50}$/tablet.

EXAMPLE 9

9.1 Preparation of Effervescent Tablets Containing Infectious Bronchitis (IB-HI20)+NDV-VH (Fowl) Live Virus SPF eggs were inoculated with IB-HI20 or with NDV-VH disease virus and incubated according to known methods for propagating of viruses in eggs.

AAF was harvested and centrifuged at 4000/g for 20 min. Lyophilization was performed fully according to known procedures.

700 mg tablets were prepared as substantially described in Example 1.

Each tablet contained 140 mg of lyophilizate.

9.2 Analysis of Tablets

When one tablet was added to 100 ml of water, dissolution was complete within 2 min, i.e. no trace of solid was visible to the naked eye.

The titer of each tablet was evaluated in SPF eggs and found to be $10^{5.80}$ and $10^{9.60}$ EID$_{50}$/tablet for IB-HI20 and NDV-VH (Fowl) respectively.

EXAMPLE 10

10.1 Preparation of Effervescent Tablets Containing Sheep Pox Live Virus

Virus propagation was performed in Vero cells grown in plastic rollers.

Lyophilization was performed fully according to known procedures.

700 mg Tablets were prepared substantially as described in Example 1.

Each tablet contained 140 mg of lyophilizate

10.2 Analysis of Tablets

The titer of each tablet was evaluated as $10^{5.85}$ TCID$_{50}$/tablet. Sheep pox vaccine's virus was titrated in Vero cells.

EXAMPLE 11

11.1 Preparation of Effervescent Tablets Containing Rinderpest Live Vaccine Virus (Cattle)

Virus propagation was performed in Vero cells grown in plastic rollers.

Lyophilization was performed fully according to known procedures.

700 mg Tablets were prepared substantially as described in Example 1.

Each tablet contained 140 mg of lyophilizate.

11.2 Analysis of Tablets

The titer of each tablet was evaluated as $10^{4.1}$ TCID$_{50}$/tablet. Rinderpest vaccine's virus was titrated in Vero cells.

11.3 Color Coding of Vaccine Compositions

Israeli Patent No. 46189 discloses poultry color-coded virus vaccine stained with a distinctive dye, which is safe in life tissues and which does not harm the viability of viruses. The different vaccines are each color-coded by means of a different distinctive dye. Suitable dyes are, for example, amaranth red dye, tartrazine yellow, indigo carmine blue or mixtures of any of these, resulting in distinctive hues.

A process of coloring the various different types of vaccines (or color-coding) of vaccines in different contrasting colors is useful against mistakes that have been made by farmers who have vaccinated their poultry flocks with a different type vaccine than the one intended, thereby exposing their unprotected flocks against the disease which they had actually intended to immunize. Such mistakes are usually discovered only too late, if at all, and in various cases have brought in complaints against the vaccine, in addition to serious financial losses and damages to the farmer. Chemical colors, however, safe as they may be by themselves, pose several problems and dangers when combined with a virus vaccine.

Vaccination of poultry involves the use of live virus vaccines in which a culture of live viruses are contained in the final product, and since live viruses are very delicate and may deteriorate easily, the technical problem is quite involved. Different coloring agents and dyes are known to be chemically active, namely they may oxygenate or reduce chemically. Live viruses are very sensitive to changes in the environment such as pH conditions, temperature, radiation, different metal ions and otherwise may be affected by chemical agents with which they come in contact. Such dyeing agents as methylene blue, or fuschin red or aniline dyes may be toxic to the viruses and possibly pose problems with the chickens or turkeys into which they would be injected. It was therefore necessary to choose such dyes that will be safe for use in live tissues and will not harm the viability of the viruses with which they are in contact. Four color shades have been chosen to identify the four most popular and important vaccines used in the poultry industry at present, namely a red color to identify Newcastle Disease vaccine of the lentogenic strain, or as it is called in Israel, the Komarov "chick" strain; a yellow color to identify the Newcastle Disease vaccine of the Komarov-Haifa or "pullet" strain; a blue color to identify the Laryngotracheitis vaccine; and a green shade to identify the Fowl Pox vaccine.

As disclosed in Israeli Patent No. 46189, different concentrations of these dyes were tried and were mixed directly with the wet vaccine before it was dispensed into the final containers and before it was desiccated (lyophilized). Several tests were run to ascertain that these dyes will not harm the vaccine.

Different batches of dyed vaccines were subjected to storage conditions under refrigeration and otherwise and repeatedly titrated to verify the virus concentration. Ample controls of the vaccine without the addition of the dyes were run parallel to every test done on the dyed vaccine. Dyed vaccines have also been tested directly on live birds to see what effect they might have. Repeat tests with all four types of vaccines and four dyes used in these experiments have shown no detrimental effect on the virus titration results. Injection trials in live birds and the application of the virus vaccines by other routes such as through the drinking water; by the stick method through the skin (Fowl Pox); and by the vent-brush method (for laryngothracheitis vaccine ) have shown that the dye had no detrimental effect on the birds and when injected intramuscularly it was reabsorbed from tissues and completely disappeared within 36 hours. Israeli Patent No. 46189 discloses vaccines tested in the field on several flocks which were vaccinated from one day of age and up to marketing age with these dyed vaccines. These birds were successfully marketed and had no evidence of the dyes whatsoever.

Further details of the invention disclosed in Israeli Patent No. 46189 may be readily understood in connection with the description given in the following examples taken therefrom, and which have been selected for the purpose of illustration only in order to enable one skilled in the art to use the color-coded formulations for vaccines, and thus are not limitations upon the invention.

EXAMPLE A

AMARANTH red dye was prepared for combination with Vineland Newcastle "chick" vaccine, by making a concentrate-dye-solution. This concentrate contained 145 grams of dry powdered dye dissolved in 4 liters of distilled water. The concentrated dye solution was autoclaved at 20 psi for 20 minutes shortly after preparation and was stored in sealed glass bottles in a dark place. The dye-concentrate solution was added at 1.33% to the final Vineland Newcastle-Chick-Vaccine.

Results of the titrations with dyed vaccine compared to undyed controlled have been found to be as follows:

| Titrations 2 weeks after lyphilization: | |
|---|---|
| without dye | $10^{9.0}$ EID 50/ml |
| with dye | $10^{9.3}$ EID 50/ml |

-continued

Accelerated titration:

| | |
|---|---|
| without dye | $10^{9.1}$ EID 50/ml |
| with dye | $10^{9.3}$ EID 50/ml |

Titration 30 days after lyophilization:

| | |
|---|---|
| without dye | $10^{9.16}$ EID 50/ml |
| with dye | $10^{9.3}$ EID 50/ml |

Titration 3 months after lyophilization:

| | |
|---|---|
| without dye | $10^{8.86}$ EID 50/ml |
| with dye | $10^{9.3}$ EID 50/ml |

Titration done 6 months after lyophilization

| | |
|---|---|
| only sample with dye | $10^{9.16}$ EID 50/ml |

EXAMPLE B

TARTRAZINE yellow dye was prepared for combination with Vineland Newcastle Pullet Strain Vaccine (The Mesogenic Haifa-Komorav Strain), by making a concentrate-dye-solution. This concentrate contained 200 grams of dry powdered dye dissolved in 3 liters of distilled water. The concentrated-dye-solution was autoclaved at 20 psi for 20 minutes shortly after preparation and was stored in sealed glass bottles in a dark place. The dye-concentrate solution was added at 3% to the final Vineland Newcastle Pullet Vaccine.

Results of the titrations with dyed vaccine compared to undyed controls have been found to be as follows:

Results of regular vaccine titration:

$10^{9.4}$ EID$_{50}$ per milliliter
Results of titrated sample with dye: $10^{8.8}$
Titration after 7 days incubation at 37° C.:

| | |
|---|---|
| without dye | $10^{8.3}$ EID 50/ml |
| with dye | $10^{8.8}$ EID 50/ml |

Titration 39 days after lyophilization:

| | |
|---|---|
| without dye | $10^{8.66}$ EID 50/ml |
| with dye | $10^{8.9}$ EID 50/ml |

Titration 93 days after lyophilization:

| | |
|---|---|
| without dye | $10^{8.66}$ EID 50/ml |
| with dye | $10^{8.66}$ EID 50/ml |

7 ½ months after lyophilization:

| | |
|---|---|
| without dye | $10^{8.53}$ EID 50/ml |
| with dye | $10^{8.76}$ EID 50/ml |

EXAMPLE C

INDIGO-CARMINE blue dye was prepared for combination with Vineland-Injections Laryngotracheitis Vaccine, by making a concentrate-dye-solution.

This concentrate contained 200 grams of dry-powdered dye dissolved in 3 liters of distilled water. The concentrate dye solution was autoclaved at 20 psi for 20 minutes shortly after preparation and was stored in sealed glass bottles in a dark place. The dye concentrate solution was added at 3% to the final Vineland Injections Laryngotracheitis Vaccine.

Results of the titrations with dyed vaccine compared to undyed controls have been found to be as follows:

Titration 3 weeks after lyophilization:

| | |
|---|---|
| without dye | $10^{6.3}$ EID 50/ml |
| with dye | $10^{6.16}$ EID 50/ml |

Accelerated titration:

| | |
|---|---|
| without dye | $10^{5.0}$ EID 50/ml |
| with dye | $10^{4.8}$ EID 50/ml |

Titration 30 days after lyophilization:

| | |
|---|---|
| without dye | $10^{6.0}$ EID 50/ml |
| with dye | $10^{5.8}$ EID 50/ml |

Titration 3 months after lyophilization:

| | |
|---|---|
| without dye | $10^{5.66}$ EID 50/ml |
| with dye | $10^{5.5}$ EID 50/ml |

Titration 7 months after lyophilization:

| | |
|---|---|
| without dye | $10^{5.5}$ EID 50/ml |
| with dye | $10^{5.6}$ EID 50/ml |

(This is a somewhat unusual drop in titre for both dyed and undyed samples and accelerated batched showed more that 1 log drop on acceleration indication possible high moisture content in this batch.)

EXAMPLE D

A green shade dye coded "P" (for Pox) was obtained by mixing INDIGO-CARMINE with TARTRAZINE dyes and was used for combination with Vineland Fowl Pox Vaccine. 100 grams of powered dye mix was dissolved in 3 liters of distilled water.

Same procedure was used as in examples No. 2 and No. 3 and the solution was added at 3% to the final Fowl Pox vaccine.

Results of the titrations with dyed vaccine compared to undyed controls have been found to be as follows:

7 days after lyophilization

| | |
|---|---|
| undyed control: | $10^{5.5}$ EID 50/ml |
| vaccine with dye: | $10^{5.5}$ EID 50/ml |

3 months later

| | |
|---|---|
| undyed control: | $10^{5.4}$ EID 50/ml |
| vaccine with dye: | $10^{5.5}$ EID 50/ml |

6 months later

| | |
|---|---|
| undyed control: | $10^{5.35}$ EID 50/ml |
| vaccine with dye: | $10^{5.4}$ EID 50/ml |

9 months after production

| | |
|---|---|
| undyed control: | $10^{3.1}$ EID 50/ml |
| vaccine with dye: | $10^{5.3}$ EID 50/ml |

SUMMARY OF THE INVENTION
(CONTINUED)

A further object of the invention is to provide a sterile package comprising a syringe containing a formulation which is compacted, compressed or tableted as a dense solid having a dissolution aid.

A further object of the invention is to provide the above sterile package, wherein the compacted, compressed or tableted solid formulation dissolves rapidly in a diluent, either within the syringe or in a separate container.

Another object of the invention is to provide a vaccine composition and method of immunizing accomplished by dissolving a solid, dense stable form of a lyophilized vaccine contained in a sterile package with a diluent to form a vaccine solution ready for administration.

A further object of the invention is to provide a lyophilized live or inactivated vaccine which is compacted, compressed or tableted as a dense, stable, solid suitable for human administration.

Another object of the invention is to provide a lyophilized live or inactivated vaccine which is compacted, compressed or tableted as a dense, stable, solid further comprising a second lyophilized component containing neutralizing antibodies against a lyophilized antigenic component.

A further object of the invention is to provide a process for producing the lyophilized vaccine containing neutralizing antibodies where the potency of the lyophilized antigenic component and the lyophilized neutralizing antibodies are separately determined to produce a vaccine formulation in a ratio for each component based on their determined potencies.

Yet another object of the invention is to provide a method of immunizing a subject in-ovo accomplished by simply dissolving a solid form of the lyophilized vaccine containing neutralizing antibodies either within a pre-packaged sterile syringe or in a separate container.

DETAILED DESCRIPTION OF THE INVENTION (CONTINUED)

This invention further provides a sterile syringe containing a stable, compressed composition, wherein the compressed composition comprises a dissolution aid.

In another embodiment, the invention provides the sterile syringe containing a stable, compressed composition having a dissolution aid, wherein the compressed composition is in the form of a hard tablet.

In a preferred embodiment, the invention provides the sterile syringe containing the hard tablet described above, wherein the hard tablet dissolves completely and rapidly in a diluent.

In a another preferred embodiment, the invention provides the sterile syringe containing the hard tablet described above, wherein the compressed composition is selected from the group consisting of an injectable hormone, drug, and vitamin.

In another embodiment, the invention provides a method of administering an injectable solution to a subject which comprises adding a diluent to any of the syringes described above to form an injectable solution in the syringe and administering the resulting solution to the subject.

This invention also provides a package comprising a stable compressed vaccine composition comprising at least one lyophilized antigenic component and a dissolution aid, wherein the package comprises a vial.

In a preferred embodiment of the invention, the vial is evacuated.

In another preferred embodiment of the invention, the vial is glass.

In a preferred embodiment of the invention, the package is a sachet.

This invention also provides a method of immunizing a subject against a disease comprising the steps of dissolving the vaccine composition which provides protection against such disease with a diluent to form a solution; and administering the resulting solution to the subject in an amount effective to immunize the subject against the disease, wherein the subject is a mammal.

In a preferred embodiment of the invention, the mammal is selected from the group consisting of a human subject, a bovine subject, and an ovine subject.

In a preferred embodiment of the invention, the antigenic component of the vaccine composition is a tetanus toxoid.

In a preferred embodiment of the invention, the mammal is a human subject and the lyophilized antigenic component of the vaccine composition is a tetanus toxoid.

This invention further provides a stable compressed vaccine composition comprising at least one lyophilized antigenic component and a dissolution aid and a second lyophilized component, wherein the second lyophilized component contains neutralizing antibodies against the lyophilized antigenic component.

In a preferred embodiment, the invention provides the stable compressed vaccine composition having the second lyophilized component containing neutralizing antibodies, wherein the antigenic component is a live virus selected from the group consisting of: Newcastle Disease virus, Infectious Bursal Disease virus, fowl pox virus, Laryngotracheitis virus, Infectious Bronchitis of poultry virus, sheep pox virus, Rinderpest virus, or an admixture of one or more of the foregoing, whether naturally occurring, recombinant or modified.

In another embodiment, the invention provides the stable compressed vaccine composition having a second lyophilized component containing neutralizing antibodies produced by the process comprising the steps of (a) lyophilizing at least one antigenic component; (b) lyophilizing neutralizing antibodies against the antigenic component separately from the antigenic component; (c) determining the potency of each of the lyophilized antigenic component and the lyophilized neutralizing antibodies; (d) mixing the lyophilized antigenic component and the lyophilized neutralizing antibodies in a ratio determined based on the potencies obtained; and (e) compressing the mixture of the lyophilized antigenic component and the lyophilized neutralizing antibodies and dissolution aids to form a stable compressed vaccine composition.

In yet another embodiment, the invention provides a method of making a stable compressed in-ovo vaccine composition comprising the steps of (a) lyophilizing at least one antigenic component; (b) lyophilizing neutralizing antibodies against the antigenic component separately from the antigenic component; (c) determining the potency of each of the lyophilized antigenic component and the lyophilized neutralizing antibodies; (d) mixing the lyophilized antigenic component and the lyophilized neutralizing antibodies in a ratio determined based on the potencies obtained, and (e) compressing the mixture of the lyophilized antigenic component and the lyophilized neutralizing antibodies and dissolution aids to form a stable compressed in-ovo vaccine composition.

In a preferred embodiment, the invention provides the above method of making a stable compressed in-ovo vaccine composition, wherein the antigenic component is a live virus selected from the group consisting of: Newcastle Disease virus, Infectious Bursal Disease virus, fowl pox virus, Laryngotracheitis virus, Infectious Bronchitis of poultry virus, Marek's Disease virus, coccidiosis or an admixture of one or more of the foregoing, whether naturally occurring, recombinant or modified.

In another embodiment, the invention provides a method of immunizing a subject in-ovo against a disease comprising the steps of (a) dissolving the stable compressed vaccine composition providing protection against the disease having the second lyophilized component containing neutralizing antibodies with a diluent to form a solution; and (b) administering the resulting solution to the subject in-ovo in an amount effective to immunize the subject against the disease with no adverse reaction.

In a preferred embodiment of the above method of immunizing a subject in-ovo, the subject is an avian subject and the disease is selected from the group consisting of Newcastle Disease, Infectious Bursal Disease, fowl pox, Laryngotracheitis, Marek's Disease virus and Infectious Bronchitis of poultry.

Further examples are presented for the preparation of human and animal tetanus toxoid vaccine compositions according to the present invention.

EXAMPLE 12

12.1 Preparation of 100 Dose Tablets Containing Tetanus Toxoid Vaccine

A liquid solution of Tetanus toxoid (Pasteur Merieux Connaught, Lot.-JJ, 4750 LF units/ml) was lyophilized in vials. The lyophilized powder was calculated to contain 47,500 LF units/gram.

One human immunization dose is 4 LF units (Micromedex Inc. Healthcare Series Vol. 107).

100 dose tablets are prepared with a single punch tableting machine such as an instrumented MANESTY F3 Single Punch 6 mm standard concave punches according to the following formulation.

Formulation:

TABLE 12

| | |
|---|---|
| Tetanus toxoid lyophilized powder | 1.85 g |
| $NaHCO_3$ anhydrous (Merck, Darmstadt Germany) | 22.9 g |
| Citric acid (Gadot, Israel) dry | 14.0 g |
| Povidone (PVP) | 1.4 g |
| Magnesium stearate | 0.1 g |

The dry ingredients, excluding the sterile tetanus toxoid, were sterilized by gamma irradiation.

The preparation tools were sterilized by steam at 121° C. and 15 PSI for 45 minutes.

The tableting powders were passed through 30 mesh and thoroughly mixed in a polypropylene bag.

Tablets of 0.2 grams were compressed by the tableting machine to a hardness of at least 2.0 SCU and immediately packed in a 10 ml sterile syringe. The syringe was immediately packed in a laminated aluminum sachet under a stream of dry, sterile nitrogen gas. The sachet was sealed and stored at 4° C.

Dissolution of the tablet was examined by opening the sachet, sucking 5 ml of sterile reverse osmosis (RO) water at a temperature of 20° C. into the syringe and pulling the piston of the syringe all the way up, the needle directed upwards to allow the gas produced in the effervescent process to be released. After the tablet was completely dissolved so that a clear suspension could be observed, the piston was pushed down to the suspension front. Dissolution time was 35 sec. with 5 mls of RO water at a temperature of 20° C. The liquid was transferred aseptically to 45 ml RO water giving a final volume of 50 ml.

EXAMPLE 13

13.1 Preparation of 10 Dose Tablets Containing Tetanus Toxoid Vaccine

A liquid solution of Tetanus toxoid (Pasteur Merieux Connaught, Lot.-JJ, 4750 LF units/ml) was lyophilized in vials and harvested in a dry sterile environment into a homogeneous pool. The lyophilized powder was calculated to contain 47,500 LF units/gram.

One human immunization dose is 4 LF units (Micromedex Inc. Healthcare Series Vol. 107). 10 dose tablets are prepared with a single punch tableting machine such as an instrumented MANESTY F3 Single Punch 6 mm standard concave punches according to the following formulation.

Formulation:

TABLE 13

| | |
|---|---|
| Tetanus toxoid lyophilized powder | 0.185 g |
| $NaHCO_3$ anhydrous (Merck, Darmstadt Germany) | 24.5 g |
| Citric acid (Gadot, Israel) dry | 14.0 g |
| Povidone (PVP) | 1.4 g |
| Magnesium stearate | 0.1 g |

The dry ingredients, excluding the sterile tetanus toxoid, were sterilized by gamma irradiation.

The preparation tools were sterilized by steam at 121° C. and 15 PSI for 45 minutes.

The tableting powders were passed through 30 mesh and thoroughly mixed in a polypropylene bag.

Tablets of 0.2 grams were compressed by the tableting machine to a hardness of at least 2.0 SCU and immediately packed in a 10 ml sterile syringe. The syringe was immediately packed in a laminated aluminum sachet under a stream of dry sterile nitrogen gas. The sachet was sealed and stored at 4° C. Dissolution of the tablet was examined by opening the sachet, sucking 5 ml of sterile RO water at a temperature of 20° C. into the syringe and pulling the leading pole of the syringe all the way up, the needle directed upwards to allow the gas produced in the effervescent process to be released. After the tablet was completely dissolved so that a clear suspension could be observed, the piston was pushed down to the suspension front.

Dissolution time was 37 sec. with 5 mls of RO water at a temperature of 20° C.

EXAMPLE 14

14.1 Preparation of Single Dose Tablets Containing Tetanus Toxoid Vaccine

A liquid solution of Tetanus toxoid (Pasteur Merieux Connaught, Lot.-JJ, 4750 LF units/ml) was lyophilized in vials and harvested in a dry sterile environment into a homogeneous pool. The lyophilized powder was calculated to contain 47,500 LF units/gram.

One human immunization dose is 4 LF units (Micromedex Inc. Healthcare Series Vol. 107).

Single dose tablets are prepared with a single punch tableting machine such as an instrumented MANESTY F3 Single Punch 6 mm standard concave punches according to the following formulation.

Formulation:

TABLE 14

| | |
|---|---|
| Tetanus toxoid lyophilized powder | 0.0185 gr |
| NaHCO$_3$ anhydrous (Merck, Darmstadt Germany) | 24.7 gr |
| Citric acid (Gadot, Israel) dry | 14.0 gr |
| Povidone (PVP) | 1.4 gr |
| Magnesium stearate | 0.1 gr |

The dry ingredients, excluding the sterile tetanus toxoid, were sterilized by gamma irradiation.

The preparation tools were sterilized by steam at 121° C. and 15 PSI for 45 minutes.

The tableting powders were passed through 30 mesh and thoroughly mixed in a polypropylene bag.

Tablets of 0.2 grams were compressed by the tableting machine to a hardness of at least 2.0 SCU and immediately packed in a 5 ml sterile syringe. The syringe was immediately packed in a laminated aluminum sachet under a stream of dry sterile nitrogen gas. The sachet was sealed and stored at 4° C.

Dissolution of the tablet was examined by opening the sachet, sucking 0.5 ml of sterile reverse osmosis (RO) water at a temperature of 20° C. into the syringe and pulling the piston of the syringe all the way up, the needle directed upwards to allow the gas produced in the effervescent process to be released.

After the tablet was completely dissolved so that a clear suspension could be observed, the piston was pushed down to the suspension front.

Dissolution time was 38 sec. with 0.5 mls of RO water at a temperature of 20° C.

As a result of the stable, compressed vaccine composition according to the present invention, a sterile package, such as a syringe, containing the vaccine tablet can be readily used in the field, thereby eliminating extra steps and materials needed to prepare the vaccine and vaccinate a subject.

The vaccine composition of the present invention provides the advantage of facilitating preparation and administration of the vaccine because its formulation allows for packaging under sterile conditions into e.g., a sterile syringe, where its dissolution can be accomplished using standard handling procedures for injectables. Consequently, once a sterile vaccine tablet according to the present invention is packed in a sterile syringe, a complete sterile route can be provided from manufacturing to administration. This provides a marked advantage over the method of packaging the tablets in blisters, where the tablet is exposed to a non-sterile environment upon contact with a diluent.

Vaccine tablets of single, as well as multiple doses can be efficiently handled in this technique.

The vaccine composition of the present invention can readily form a vaccine suitable for parenteral administration, which allows the vaccine composition to be not only a live vaccine, but also an inactivated one. For example, as stated above, dead vaccine components can be either, an inactivated whole cell or virus, a subunit vaccine, either recombinant or a non-genetically modified one, or a toxoid.

The above suggested methods are suitable for animal as well as human prophylaxis.

In addition, packaging of the vaccine composition of the present invention, for example, in the form of a tablet in a sterile package, e.g. a syringe, for storage and subsequent dissolution and administration by injection is not only suitable for vaccination material. This technique can be used for other injectables such as hormones, drugs, vitamins, etc.

The methods described in the specification to produce a stable, compressed composition contained in a sterile package provide the following manufacturing benefits: the active material is accurately examined/analyzed prior to compression or tableting, the distribution of the tablets into, for example, open syringe cylinders is easily accomplished in a continuous process and many materials can be compressed into the tablet in a compacted volume. Lyophilized materials can be included in the tablet and can keep their characteristics as shown in the above examples. Moreover, a dissolution aid is added to the composition, such as in the case of effervescent tablets to allow for complete and/or rapid dissolution with no major effect on the active materials.

The syringes filled with the tablets can be packed into a sachet under dry, sterile nitrogen gas. This ensures a prolonged shelf life of the product.

The above description is for the purpose of teaching the person of ordinary skill in the art how to practice the invention, and is not intended to detail all those obvious modifications and variations of it, which will become apparent to the skilled worker upon reading the description. It is intended, however, that all such obvious modifications and variations be included within the scope of the present invention, which is defined by the following claims.

What is claimed is:

1. A stable compressed vaccine composition consisting essentially of a lyophilized antigenic component, a second lyophilized component, and a dissolution aid, wherein the second lyophilized component contains neutralizing antibodies against the lyophilized antigenic component.

2. The stable compressed vaccine composition of claim 1, produced by the process comprising the steps of:

(a) lyophilizing an antigenic component;

(b) lyophilizing neutralizing antibodies against the antigenic component separately from the antigenic component;

(c) determining the potency of each of the lyophilized antigenic component and the lyophilized neutralizing antibodies;

(d) mixing the lyophilized antigenic component and the lyophilized neutralizing antibodies in a ratio determined based on the potencies obtained in step (c); and (e) compressing the mixture of the lyophilized antigenic component and the lyophilized neutralizing antibodies with at least one dissolution aid to form a stable compressed vaccine composition.

3. A method of immunizing an avian subject in-ovo against a disease comprising the steps of:

(a) dissolving the vaccine composition of claim 1 which provides protection against such disease with a diluent to form a solution; and (b) administering the resulting solution to the subject in-ovo in an amount effective to immunize the subject against the disease with no adverse reaction.

4. The method of claim 3, wherein the disease is selected from the group consisting of Newcastle Disease, Infectious Bursal Disease, fowl pox, Laryngotracheitis, Marek's Disease virus, coccidiosis and Infectious Bronchitis of poultry.

5. The stable compressed vaccine composition of claim 1, wherein the antigenic component is a live virus selected from the group consisting of: Newcastle Disease virus, Infectious Bursal Disease virus, fowl pox virus, Laryngotracheitis virus, Infectious Bronchitis of poultry virus, sheep pox virus, Rinderpest virus, or an admixture of one or more of the foregoing, whether naturally occurring, recombinant or modified.

6. The stable compressed vaccine composition of claim 1, wherein the lyophilized antigenic component of the vaccine composition is a tetanus toxoid.

7. A method of immunizing a human against tetanus toxoid comprising the steps of:
(a) dissolving a stable compressed vaccine composition which provides protection against tetanus toxoid having at least one lyophilized antigenic tetanus toxoid component and a dissolution aid with a diluent to form a solution; and
(b) administering the resulting solution to the human in an amount effective to immunize the human against tetanus toxoid.

8. A stable compressed vaccine composition consisting of a lyophilized antigenic component, a second lyophilized component, and a dissolution aid, wherein the second lyophilized component contains neutralizing antibodies against the lyophilized antigenic component.

9. The stable compressed vaccine composition of claim 8, produced by the process comprising the steps of:
(a) lyophilizing at least one antigenic component;
(b) lyophilizing neutralizing antibodies against the antigenic component separately from the antigenic component;
(c) determining the potency of each of the lyophilized antigenic component and the lyophilized neutralizing antibodies;
(d) mixing the lyophilized antigenic component and the lyophilized neutralizing antibodies in a ratio determined based on the potencies obtained in step (c); and
(e) compressing the mixture of the lyophilized antigenic component and the lyophilized neutralizing antibodies with at least one dissolution aid to form a stable compressed vaccine composition.

10. A method of immunizing an avian subject in-ovo against a disease comprising the steps of:
(a) dissolving the vaccine composition of claim 8 which provides protection against such disease with a diluent to form a solution; and
(b) administering the resulting solution to the subject in-ovo in an amount effective to immunize the subject against the disease with no adverse reaction.

11. The method of claim 10, wherein the disease is selected from the group consisting of Newcastle Disease, Infectious Bursal Disease, fowl pox, Laryngotracheitis, Marek's Disease virus, coccidiosis and Infectious Bronchitis of poultry.

12. The stable compressed vaccine composition of claim 8, wherein the antigenic component is a live virus selected from the group consisting of: Newcastle Disease virus, Infectious Bursal Disease virus, fowl pox virus, Laryngotracheitis virus, Infectious Bronchitis of poultry virus, sheep pox virus, Rinderpest virus, or an admixture of one or more of the foregoing, whether naturally occurring, recombinant or modified.

13. The stable compressed vaccine composition of claim 8, wherein the lyophilized antigenic component of the vaccine composition is a tetanus toxoid.

* * * * *